United States Patent [19]

Zachry

[11] Patent Number: 5,112,325
[45] Date of Patent: May 12, 1992

[54] SURGICAL SPONGE WITH PLURALITY OF RADIOPAQUE MONOFILAMENTS

[75] Inventor: Kathy W. Zachry, Kingston, Tenn.

[73] Assignee: DeRoyal Industries, Inc., Powell, Tenn.

[21] Appl. No.: 312,029

[22] Filed: Feb. 17, 1989

[51] Int. Cl.⁵ .............................................. A61F 13/36
[52] U.S. Cl. ..................................... 604/362; 604/367; 604/384
[58] Field of Search ............... 604/362, 365, 367, 371, 604/384; 128/654, 656, 658

[56] References Cited

U.S. PATENT DOCUMENTS

| | | | |
|---|---|---|---|
| 4,205,680 | 6/1980 | Marshall | 604/362 |
| 4,244,369 | 1/1981 | McAuinn et al. | 604/366 |
| 4,557,264 | 12/1985 | Hinsch | 606/231 |
| 4,639,253 | 1/1987 | Dyer et al. | 604/362 |
| 4,718,897 | 1/1988 | Elves | 604/362 |

*Primary Examiner*—Randall L. Green
*Assistant Examiner*—D. Willse
*Attorney, Agent, or Firm*—Luedeka, Hodges, Neely & Graham

[57] ABSTRACT

A surgical sponge, particularly of the neurosurgical class, comprising a fibrous web having attached to one surface thereof a locator string comprising a bundle of X-ray detectable monofilaments that are helically overwrapped as by a yarn. One or more of the components of a preferrred string is bondable to the web by means of heat and/or pressure.

2 Claims, 1 Drawing Sheet

SURGICAL SPONGE WITH PLURALITY OF RADIOPAQUE MONOFILAMENTS

FIELD OF THE INVENTION

This invention relates to surgical sponges and especially to such sponges used in neurosurgical procedures. More particularly, this invention relates to surgical sponges which have associated therewith an x-ray detectable element and a locator string.

BACKGROUND OF THE INVENTION

Medical sponges, and particularly neurological sponges, commonly comprise a fibrous web, the fibers of which may be cotton, rayon, polyester or other synthetic or a combination of these. The fibers are bonded one to another by mechanical and/or chemical bonds, either with or without bonding additives. Neurological sponges, generally are of two types, strung and unstrung. In the strung sponges the absorbent web commonly is relatively small, ranging from about ¼ inch square upwards. Most such sponges are less than about 3 inches in length and about 3 inches wide. The webs commonly are of about 1/32 inch thick. The strung sponges have attached thereto one or two strings, commonly a textile thread having one of its ends anchored to the web and the remainder of the string extending from the web to serve as a locator element. The unstrung sponges most often are larger than the strung sponges, ranging up to 6 inches in length and 3.5 inches in width. These sponges have no depending string attached thereto.

Neurological sponges are employed for absorbing blood and body fluids, but most frequently are saturated with saline or other solution and used to protect tissue or applied to the tip of a suction device for protecting the tissue when suction is applied.

In the course of a surgical procedure, the medical sponges are supplied to the operating room table in units of 10 and are carefully counted before and after use. Because absorbent sponges very closely resemble tissue when the sponge is soaked with blood, it is at times difficult to distinguish the small blood-soaked sponge from the surrounding body tissue. Thus, it is common practice to attach to the sponge a locator string, commonly about 12 inches in length, of a textile material, for example, such string being kept at all times outside the surgical incision so that the presence of the sponge may be readily noted through observing the string. These sponges further are provided with a separate and distinct x-ray opaque element fixed to the sponge in a manner as prevents its dislodgement. In the event the count of the sponges following the surgery indicates that one or more of the sponges is missing and a search of the operating room fails to locate the missing sponge, while the patient is still in the operating room, a portable x-ray unit may be brought in and the surgical site x-rayed in an attempt to determine whether the sponge has been left inside the patient.

Heretofore, neurological sponges have been provided with one or more x-ray opaque elements comprising a polyvinylchloride or polypropylene impregnated with barium sulfate. The prior art teaches attachment of such element(s) to the web by heat bonding or stitching of the element to the web. These same prior art sponges also may be provided with a separate locator string which is either heat bonded or stitched to the web. One such locator string in the prior art is a polyester textile yarn which is heat bonded to the web employing ultrasonic welding techniques. These prior art strings are not radiopaque.

One of the major problems of the prior art neurological sponges is that the small size of the web dictates that the element be no longer in length than the longest dimension of the web. The width of the element desirably is kept as small as possible so as to not reduce the absorptive area of the sponge. It will be appreciated that in the smaller sponges, the area of bond between the x-ray detectable element and the web can occupy a very substantial percentage of one surface of the web. Such small x-ray detectable elements of the prior art make the sponge most difficult to locate with an x-ray unit. This is especially true when it is recalled that the x-ray unit used in an operating room is a portable unit and therefore commonly does not have the high resolution that is desirable when seeking small radiopaque objects. Still further, should the prior art sponge be located inside the patient and oriented "on edge" as presented to the X-ray unit, or behind a bony protuberance, etc. the small size of the x-ray detectable element may cause it to go undetected.

Further, because of the sensitive nature of brain tissue, the presence of the X-ray detectable element in or on a neurological sponge cannot be rough or physically irritating and cannot appreciably detract from the pliability of the sponge especially when wetted. In the prior art it has been suggested to use soft and pliable vinyl or polypropylene-based elements that are impregnated with barium sulfate as X-ray detectable elements. This material is rubbery, stretches readily, and has relatively little tensile strength when formed into thin strips or monofilaments. When bonded to a fibrous pad, however, the monofilamentary nature of the element flattens and stiffens with the result that the sponge loses an appreciable portion of its flexibility. To be effective as a radiopaque element, the size of the element must be sufficient to develop a detectable image. Thus, in the prior art the size of the monofilamentary elements and its expanded, flattened configuration when bonded to the web has both consumed an undesirably large percentage of the area of the web and introduced undesirable stiffness to the web. This is particularly true when the bond of the element to the pad is effected by ultrasonic welding as employed in the prior art, or when the element is in a continuous unitary form.

In larger sponges, e.g. laparotomy gauze sponges, the prior art has included a hollow tubular sheath loop element housing a monofilament of radiopaque material attached to one corner of the sponge and serving as a retrieval loop, plus as an aid in detecting the sponge with a x-ray unit. Such sheaths are relatively bulky and are themselves of a diameter that is equal to or greater than the small neurosponges. In any event, such loops are too large, too stiff, and too abrasive for use with neurosponges. They are attached to the gauze sponge by stitching which is generally unacceptable in neurosponges.

Accordingly, it is an object of the present invention to provide a medical sponge, particularly of the neurological class, which is more readily detectable when subjected to X-ray examination. It is another object of the present invention to provide a medical sponge including an X-ray detectable element and a locator string in which the absorptive area of the sponge is maximized. It is another object of the present invention to provide a novel locator string for surgical devices.

Other objects and advantages of the present invention will be recognized from the description contained herein, including the figures in which:

SUMMARY OF THE INVENTION

Figure 1:
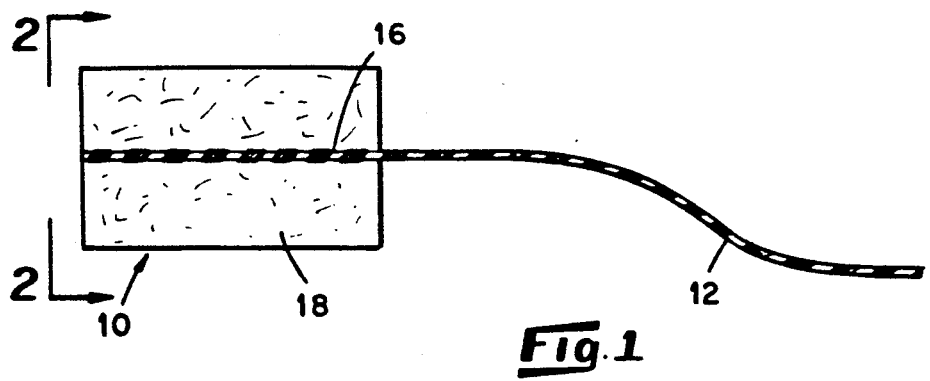
FIG. 1 is a representation of a strung neurological medical sponge in accordance with the present invention.
Figure 2:
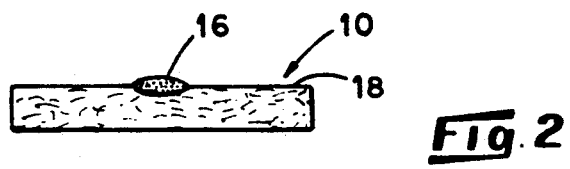
FIG. 2 is an enlarged cross-sectional view of the sponge of FIG. 1 taken along the line 2—2 of FIG. 1.

Stated briefly, the present inventors have found that an improved medical sponge, particularly a sponge of the neurological class, is obtainable by means of a plurality of X-ray detectable elements integrated into a locator string and attached to a web of absorbent fibers employing a common location of attachment. The preferred locator string of the present sponge comprises a bundle of monofilamentary polymeric fibers impregnated with barium sulfate or equivalent x-ray opaque material with the bundle being overwrapped, preferably helically, with at least one yarn such as a polyester textile yarn. In one embodiment, this string is about 12 inches long. One end of the string is bonded to the web with the remainder of the string depending from the web. Importantly, the X-ray detectable portion of the string preferably extends the full length of the string so that when viewed under X-rays, the string appears as a nonlinear, i.e. serpentine, member and is readily detectable and distinguishable from the usual human body elements. Because the string includes the X-ray detectable component therein, a single bonding location is employed in attaching the string to the web, thereby minimizing that area of the web which is taken up in the bond and therefore not available for absorbing fluids.

In a preferred embodiment, the bond between the string and web is effected in a manner such that the X-ray detectable monofilaments of the string retain their individuality, hence are movable relative to one another to prevent appreciable reduction of the flexibility of the web in the area of the bond.

DETAILED DESCRIPTION OF THE INVENTION

With reference to the several figures, the preferred embodiment of the present sponge comprises an absorbent fibrous web 10 to which there is attached a locator string 12 that has incorporated therein a plurality of monofilamentary X-ray detectable elements 14. One end 16 of the string is secured to one surface 18 of the web with the remainder of the length of the string depending from the web.

In the depicted embodiment, the web 10 is formed of highly absorbent fibers, such as medical grade rayon fibers, which are bonded into a coherent body by chemical and/or mechanical bonds. Chemical bonds may be developed by the inherent nature of the fibers, for example by reason of their electric charge, or the chemical bonds may be developed by the use of an additive, for example an acrylic resin or other like additive. Mechanical bonding of the fibers of the web one with another may also, or alternatively, be developed in the course of formation of the web due to entanglement of the fibers with one another, by mechanically pressing the web to compact the fibers, and/or by other means such as pressure-entanglement of the web fibers. In any event, the bonding of the fibers within the web is preferably sufficient to cause the fibers to remain in the web when the web is wetted and/or undergoes a slight abrading action when used to wipe tissue or the like. In the art, this characteristic of the web is termed "non-linting" and is understood to refer to the situation where there is a minimum of fibers dislodged from the web during use and not to an absolute absence of dislodged fibers. In the manufacture of the sponge, the web may assume any of several geometries, such as squares, rectangles and, on occasion, round or oval geometries. The thickness of the web is not critical so long as it remains sufficiently flexible to serve as a wipe or is not so thick or thin as to prevent it to serve as a permeable cover for the tip of a suction device. Thicknesses of about 1 mm up to about 3 mm are commonly used.

The locator string 12 of the present invention is of importance in the present invention. The preferred string comprises a bundle 20 of individual polymeric, e.g. polypropylene, monofilaments 14, each impregnated with barium sulfate, and having an individual size of between about 75 and about 95 denier. It has been found that between about 20 and about 50, preferably about 40, monofilaments aligned substantially parallel to one another provide a bundle of a size, diametrically, that is readily detected by the usual portable X-ray unit, and provide sufficient volume for receiving an overwrapping textile yarn 22 to form a coherent string of appropriate tensile strength. In the present invention, the barium sulfate is preferably present in amounts of about 60% wt/wt of the polypropylene. It is recognized, however, that other concentrations of barium sulfate may be employed but such may require adjustment of the number of monofilaments that are suitable to provide the desired opacity to X-rays. In any event, the preferred X-ray detectable element is capable of being bonded by heat and/or pressure with the fibrous structure of the web, at least on the surface of the web.

By reason of the multiple monofilaments employed in the present locator string, the string is provided with excellent flexibility. Thus, the string is not so stiff as to interfere with the placement or other use of the sponge by the surgeon, as compared to the relative stiffness of a monofilament of polypropylene or like polymeric material that has sufficient volume to permit it to be detectable with a portable X-ray unit. The present multifilament bundle further introduces a "cable" effect to the string wherein the several monofilaments tend to support one another with the result that the combination exhibits a greater tensile strength than a monofilament of the same material and of equal diameter.

The overwrapping yarn 22 binds the bundle 20 and enhances the tensile strength of the string. It may be of cotton, polyester or other medically acceptable material that provides the requisite strength and which does not impart a deleterious roughness to that surface of the web to which the string is attached. For these and other reasons, the preferred yarn is fibrous, such as spun-bonded polyester, as opposed to monofilamentary, inasmuch as fibrous strings have been noted to be more soft than monofilaments. The preferred yarn 22 is of a size of between about 450 and about 550 denier, and most preferably about 500 denier. Further, the preferred yarn is twisted with about 2 to 5 turns per inch to enhance its strength and to aid in developing its coherency. In the preferred embodiment, the yarn is wrapped in helical fashion about the circumference of the bundle 20 of monofilaments, employing between about 4 and about 11 and preferably about 9.5, turns per inch of the length of the bundle. For use in the present sponge, the completed string is cut into individual lengths of about 12 inches. Other lengths may be employed, but 12 inches has been found to be the length most accepted by surgeons. This length of string also has been found to provide a volume of X-ray detectable material that is readily discernible from body tissue and/or other body parts such as bony protuberances, etc. In performing the cut of the string to length, preferably a hot knife or the like is employed so as to affect a fusion of the ends of the monofilaments and the yarn and thereby prevent unravelling of the yarn from its encircling relationship to the bundle of monofilaments. The preferred composite locator string as disclosed herein has a minimum breaking load of at least about 4.0 lbs. and preferably 4.4 lbs. or greater; a mean extension of about 400%; and a tenacity of about 5 g/denier or greater.

The use of a single overwrapping yarn is preferred so as to minimize the stiffening effect of the yarn upon the composite string and to keep the diametral dimension of the string within the preferred range. Multiple wrapping yarns may be employed, using a single or multiple helical wrap pattern. In this regard, it is noted that the yarn 22 preferably is wound helically about the circumference of the bundle sufficiently tightly to ensure that the multiple filaments are closely and firmly bound into the desired bundle configuration. As noted, between about 4 and 11 turns of the single yarn about the bundle per each lineal inch of the bundle imparts the required coherency of the bundle with minimum presence of the yarn.

In assembling the string and web, one end 16 of the string is securely attached to one surface 18 of the web 10 as by heat-pressure bonding. One suitable bonding method is ultrasonic welding. This method is preferred because it readily lends itself to efficient manufacturing, provides a strong bond without causing the bonded area to occupy an undue area on the surface of the web, and is economical, among other things. Because of the relatively small size of the webs employed in many neurological sponges, preferably that end of the string attached to the web extends across a full dimension, i.e. width or length, of the web to ensure maximum strength of the bond of the string to the web. It is recognized that the length dimension of this bond may not extend across a full dimension of the web, but in any event, it is important to ensure that the bond is adequate to preclude the string from pulling away from the web when the web is in use, and when the web is saturated with liquid. Notably, in the present sponge, there is a single line of attachment of the string to the web. This reduces the area of the surface of the web occupied by the bond, thereby maximizing the absorptivity of the sponge. Such bonding is permissible due to the fact that the present inventors combine the x-ray opaque element as an integral part of the locator string. These two components are not only compatible in the present sponge, but provide a synergistic effect in the formation of the bond between the string and the web. Specifically, each of the preferred components of the locator string, i.e. polypropylene and polyester, are thermoplastic and each contributes to the formation of the bond to the web when the string is subjected to heat and/or pressure sufficient to cause these components to soften and bond with the fibers of the web. As noted, ultrasonic welding serves most satisfactorily for effecting the bond.

Notably, in the preferred bond, the joinder of the string and the web takes place principally and substantially exclusively at the interface between that portion of the string that is in contact with the web surface. This results in a bond wherein a minimum of the web fibers are caused to be bonded to one another or to the string, and a minimum of the volume of the string is joined to the web fibers, so that a maximum of the X-ray detectable monofilaments retain their individuality, at least throughout a major portion of the string in the bond area, so that these monofilaments are relatively freely movable, i.e. shiftable, relative to one another to thereby ensure minimum deleterious stiffening of the sponge in the bond area.

Figure 5:
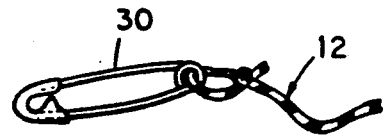
FIG. 5 is a representation of a locator string in accordance with the present invention tied to a small item used in surgery.
Figure 3:
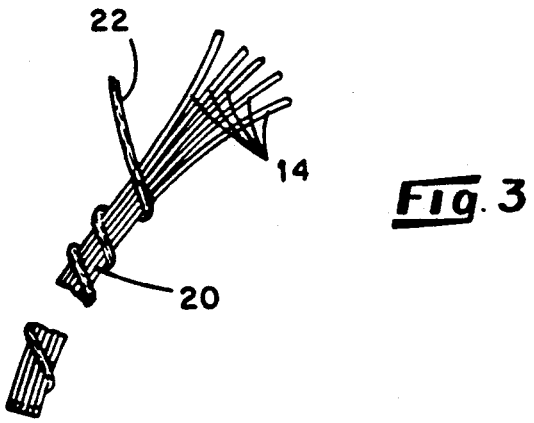
FIG. 3 is a representation of a portion of a locator string as employed in the sponge of FIG. 1 and showing one end of the string partially unravelled to show the multifilamentary nature of the string and other features of its construction, only 5 monofilaments being shown for reasons of clarity.
Figure 4:
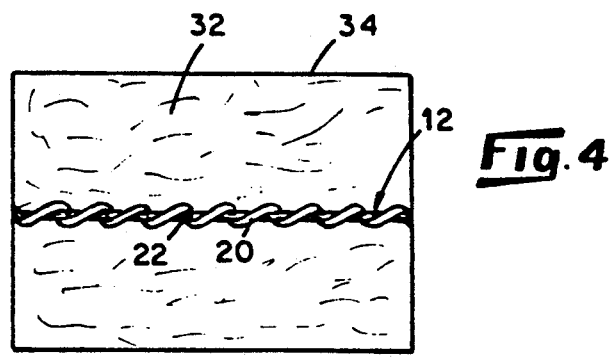
FIG. 4 is a representation of an unstrung neurosurgical medical sponge, in plan view, in accordance with the present invention.

Whereas the locator string has been described herein in connection with its use in combination with a web to provide a neurosurgical sponge, it is recognized that the locator string may also be employed as a radiopaque locator element in combination with other surgical devices. For example, the locator string is useful for tying a length thereof to any of the several small items at times used in surgery such as safety pins 30 (FIG. 5), fishhook retractors, etc. In a further embodiment, a length of the present locator string 12 may be bonded to one surface 32 of a fibrous sponge 34 with no substantial portion of the string extending beyond the borders of the sponge, as depicted in FIG. 4.

Whereas the present invention has been described herein in specific embodiments, it is recognized that other equivalent embodiments are possible and it is intended to limit the invention only as set forth in the appended claims.

What is claimed:

1. A medical sponge comprising an absorbent web and a locator string attached to a surface thereof, said locator string comprising a plurality of individual radiopaque monofilaments assembled into an elongated bundle and a yarn encircling the circumference of said bundle and gathering the monofilaments into a coherent elongated member wherein the attachment between said locator string and said web extends substantially across one full dimension of said web.

2. A medical sponge comprising an absorbent web and a locator string attached to a surface thereof, said locator string comprising a plurality of individual radiopaque monofilaments assembled into an elongated bundle and a yarn encircling the circumference of said bundle and gathering the monofilaments into a coherent elongated member wherein said locator string is attached to said web by means of a bond therebetween that is developed by heat and pressure.

* * * * *